(12) United States Patent
Buchanan

(10) Patent No.: US 7,993,138 B2
(45) Date of Patent: Aug. 9, 2011

(54) APEX LOCATOR FOR ENDODONTIC PROCEDURES

(76) Inventor: L. Stephen Buchanan, Santa Barbara, CA (US)

( * ) Notice: Subject to any disclaimer, the term of this patent is extended or adjusted under 35 U.S.C. 154(b) by 125 days.

(21) Appl. No.: 12/194,477

(22) Filed: Aug. 19, 2008

(65) Prior Publication Data

US 2009/0053666 A1   Feb. 26, 2009

Related U.S. Application Data

(60) Provisional application No. 60/957,092, filed on Aug. 21, 2007.

(51) Int. Cl.
*A61C 5/02* (2006.01)
*A61B 5/103* (2006.01)
(52) U.S. Cl. ........................ 433/224; 600/590
(58) Field of Classification Search .................. 433/224, 433/81, 29; 600/589, 590
See application file for complete search history.

(56) References Cited

U.S. PATENT DOCUMENTS

| | | | |
|---|---|---|---|
| 5,112,224 A | | 5/1992 | Shirota |
| 5,305,181 A | * | 4/1994 | Schultz ............... 361/679.03 |
| 5,752,827 A | * | 5/1998 | Baron et al. ............... 433/68 |
| 7,139,016 B2 | * | 11/2006 | Squilla et al. ............... 348/66 |
| 7,695,469 B2 | * | 4/2010 | Boutoussov et al. ............ 606/13 |
| 2008/0187880 A1 | * | 8/2008 | Becker et al. ............... 433/25 |

FOREIGN PATENT DOCUMENTS

| | | |
|---|---|---|
| JP | 10155817 | 6/1998 |
| JP | 10165424 | 6/1998 |
| JP | 10179657 | 7/1998 |
| WO | WO 2005/115271 | 12/2005 |
| WO | WO 2008/096347 | 8/2008 |
| WO | PCT/US2008/001009 | 11/2008 |

* cited by examiner

*Primary Examiner* — John J Wilson
(74) *Attorney, Agent, or Firm* — Koppel, Patrick, Heybl & Philpott; Michael J. Ram

(57) ABSTRACT

An electronic device for locating the apex of a root canal within a tooth of a dental patient has a display screen on a display component to provide an image indicating when the apex of a root canal has been located. A free end of a first electrical lead is provided for placement within the root canal or in contact with an electrically conductive tool within the root canal. A free end of a second electrical lead is used to establishing a ground on a conductive portion of the dental patient such as a tissue surface within the mouth. The opposite ends of each of the leads is connected to the display component. Removeably attached to the display component is a lead carrier. The detachable lead carrier and the leads mounted thereon can be sterilized as a unit and then attached to the display component, which is bagged in a sterile barrier, for performing the apex locating procedure. The apex locator has one or more mounting structures for placing the display in a location adjacent the patients head, attached to adjacent instrumentation, or attached to the dental practitioner's hand or arm such that the display image is readily visible by the dental practitioner during the apex locating procedure.

3 Claims, 6 Drawing Sheets

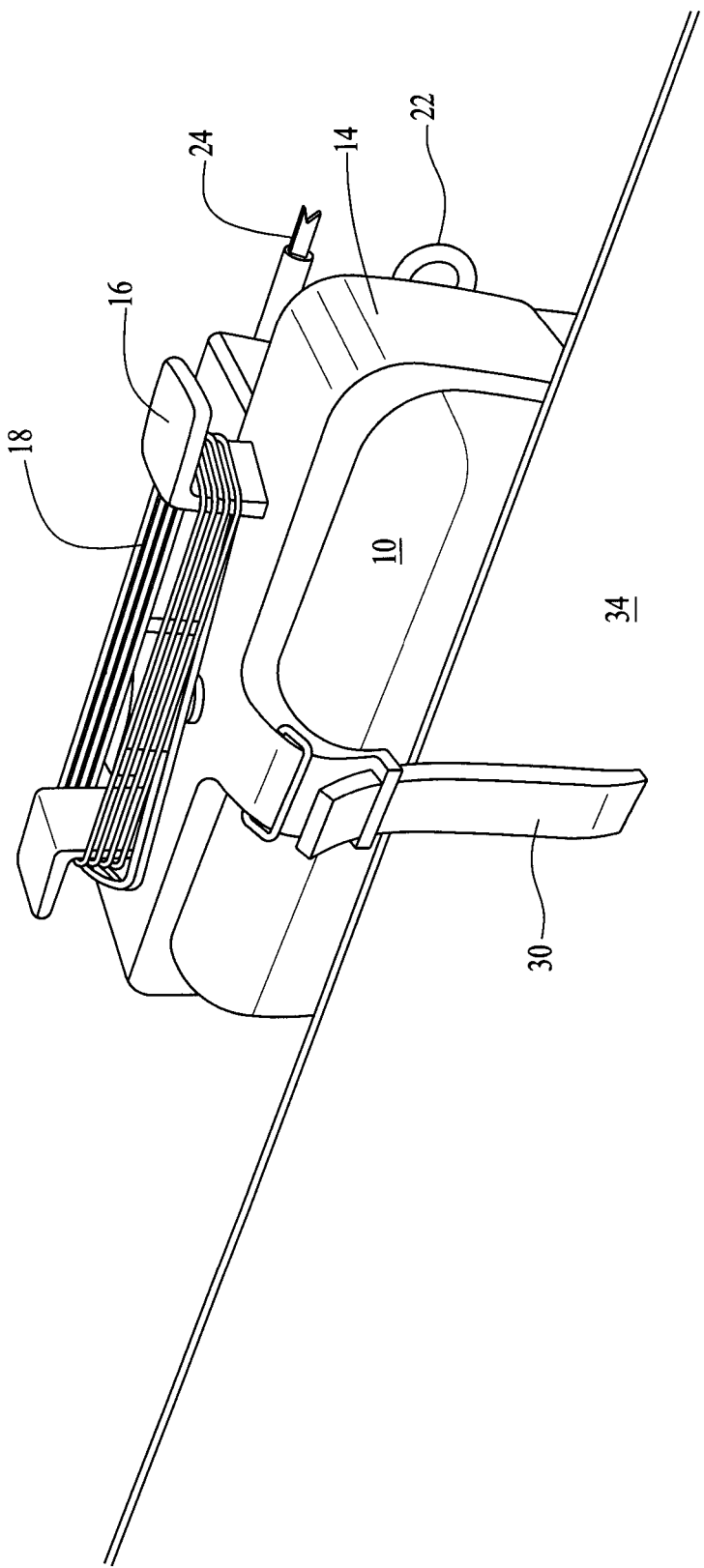

APEX LOCATOR FOR ENDODONTIC PROCEDURES

This application claims the benefit of U.S. Provisional Application No. 60/957,092 filed Aug. 21, 2007.

BACKGROUND

Endodontics, a specialty of the field of dentistry, relates to the diagnosis and treatment of diseases of the dental pulp tissues residing in teeth. When pulp in a tooth becomes diseased and must be treated to retain that tooth in the patient's mouth, it is necessary to enter the pulp chamber, locate each of the canals contained in the tooth's root structure, and to pass endodontic instruments, called files, through each canal to it's end point, the apical foramen (the apex). During this initial negotiation of the canal spaces and during the procedures that follow, which include the shaping, cleaning, and filling of those canals it is critical to determine the exact endpoint of these spaces so that none of the infected canal space is left untreated or that surplus filling materials are not pushed through the ends of the root canal, both outcomes being risks for failure of treatment and loss of the tooth at some later time.

When root canal therapy began as an accepted procedure, in the late 1800's, dental x-rays were used to determine the lengths of canals by placing a root canal instrument into each canal, taking an x-ray image of it in place, and then measuring the discrepancy of the file length from the end of the canal to back figure it's length. This method of length determination was the only way to accomplish this important objective until the 1960's when Sunada invented an electronic method of length determination by recognizing that root structure was relatively non-conductive whereas the tissues of the patient's jaw at the end of these apical foramina was conductive. This enabled the end point of the canal to be found by measuring currents between a ground lead on the patient's lip and a lead touching the shank of a root canal file placed to the end of the canal space. When this electronic device, essentially an ohm meter, was hook up, it would register little or no current flow while the file tip was within the root space of the tooth but would show a current flow when the file tip approached and passed the apical foramen on it's way toward the tissues surrounding the end of the canal.

This method of length determination, known as electronic apex location, is currently the most accurate and efficient way to determine the length of a root canal, because the exit points of root canals are often not visible on dental x-rays. Also, this procedure eliminates the time consuming process of capturing and developing a radiographic image in the middle of treatment. However, there are several challenges associated with current apex locator designs and the ability to effectively prepare and use these devices in the operative environment.

The greatest challenge is the management of the electronic leads necessary in its operation. These leads must be autoclaved between patients to prevent cross-contamination from infectious products, they must be kept off of contaminated surfaces in the dental operatory, and they must be kept untangled from the many other cords and cables in the operative site. Furthermore, it is necessary to shield the apex locator in barrier material as it cannot be autoclaved like the lead set. Currently no apex locator is designed to facilitate autoclaving of leads and wrapping of the electronic control unit in a simple, efficient manner.

A second challenge is positioning of apex locator display in the operatory as counter space is limited, each dentist has a different operatory configuration, and the display must be easily seen by the dentist during initial instrumentation procedures.

The device described herein resolves each of these issues in a simple, cost effective, and procedurally ideal manner.

BRIEF DESCRIPTION

The apex locator set forth herein is miniaturized, showing only the pertinent data on the display. Most of the existing apex locator devices have large graphical displays that are visually attractive but unnecessary in achieving the objective of locating the end point of the canal. The smaller display requires a smaller size case because a small display is needed and a smaller battery pack is needed for the more energy efficient display. Size is an underappreciated issue in the dental environment. Most apex locators on the market have a footprint of twenty square inches, which is valuable space taken away from the countertop that could better be used for instruments and materials need in the endodontic procedure.

Besides the described units being smaller, the small size allows the clinician to place the display device in a readily visible location right next to the patient's head. The design, with a single multi-use attachment, allows dentists to place the miniaturized device on the dentist's wrist, clipped to the patient bib, attached magnetically to another device in the operatory such as a microscope or x-ray view box, or even, with the fold out stand deployed, on the countertop if necessary.

Furthermore, this detachable device has a cord caddy around which the two leads are wrapped and a clip to secure each of the lead tips. This detachable device is easily placed in an autoclave bag for sterilization, and clips over the apex locator control device allowing placement of a zip-lock bag around the device to act as a barrier to bacterial contaminants. Furthermore, this cord management system allows the plugs on the lead set to become automatically attached when it is clipped onto the apex locator and automatically become unplugged when the caddy is removed for sterilization.

BRIEF DESCRIPTION OF THE DRAWINGS

FIG. 6 is a rear perspective view showing the device of FIG. 1 attached to a drape.

DETAILED DESCRIPTION

Figure 1:
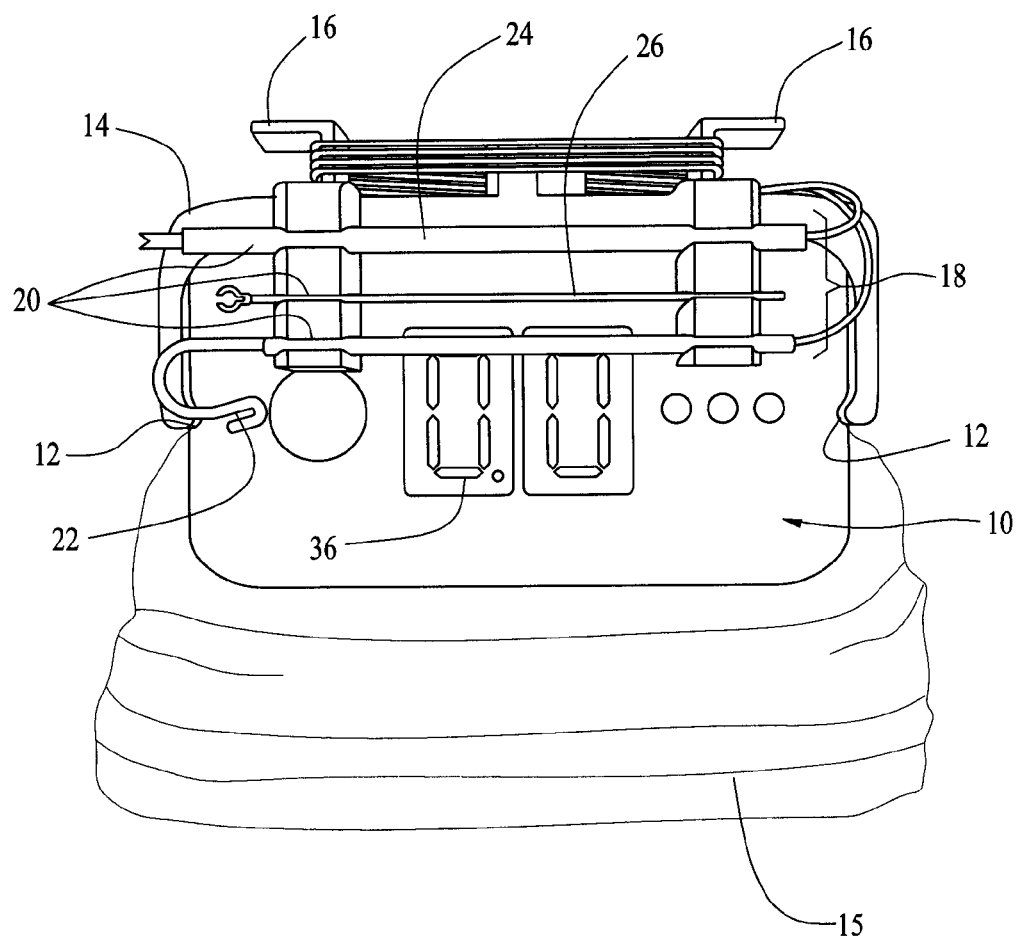
FIG. 1 is a front view of the apex locator showing the display, leads and sensing tools and lead holder.
Figure 2:
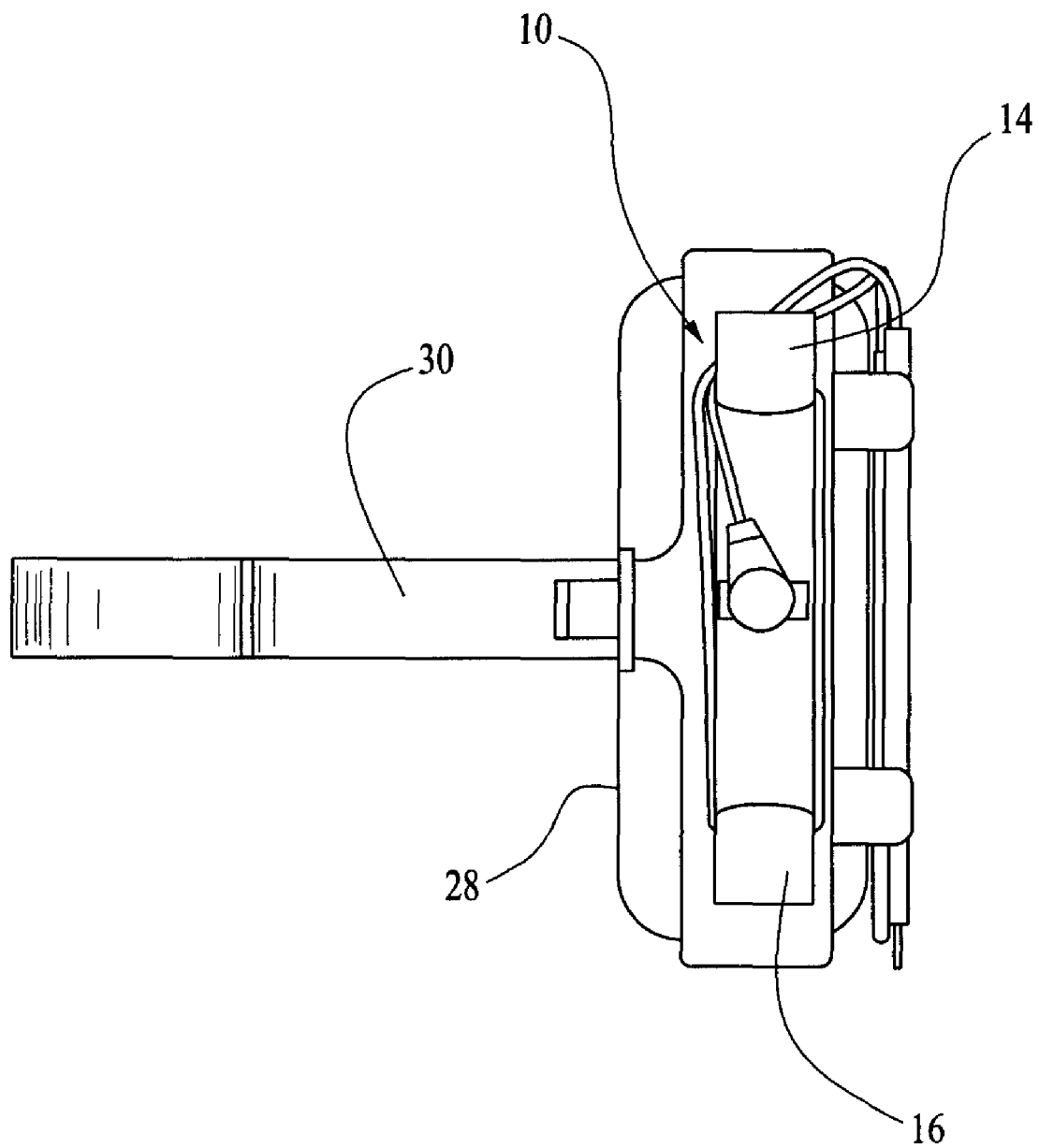
FIG. 2 is a top view of the apex locator of FIG. 1.
Figure 3:
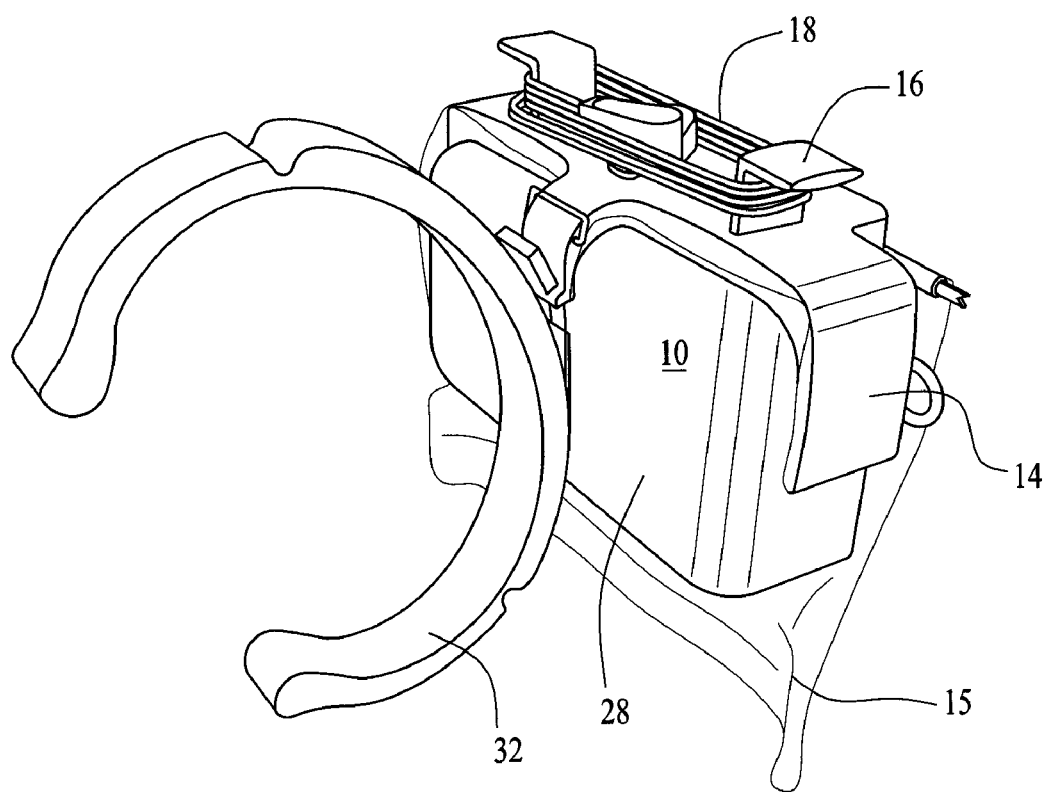
FIG. 3 is a rear perspective view of the apex locator of FIG. 1 showing a clip for wrist mounting.
Figure 4:
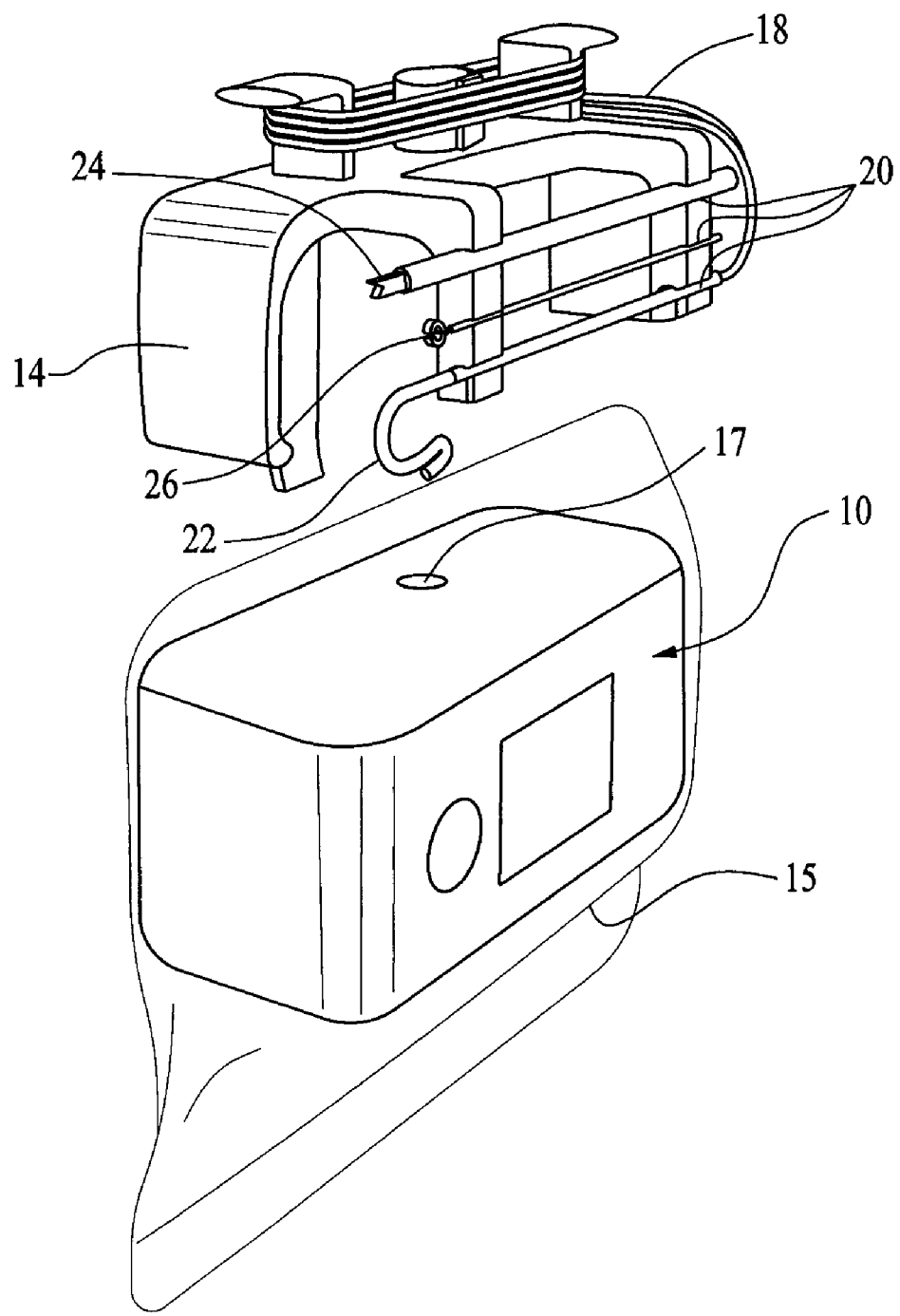
FIG. 4 is a front perspective exploded view showing the display unit in a plastic sterilization bag, the display unit separated from the caddy stand.
Figure 5:
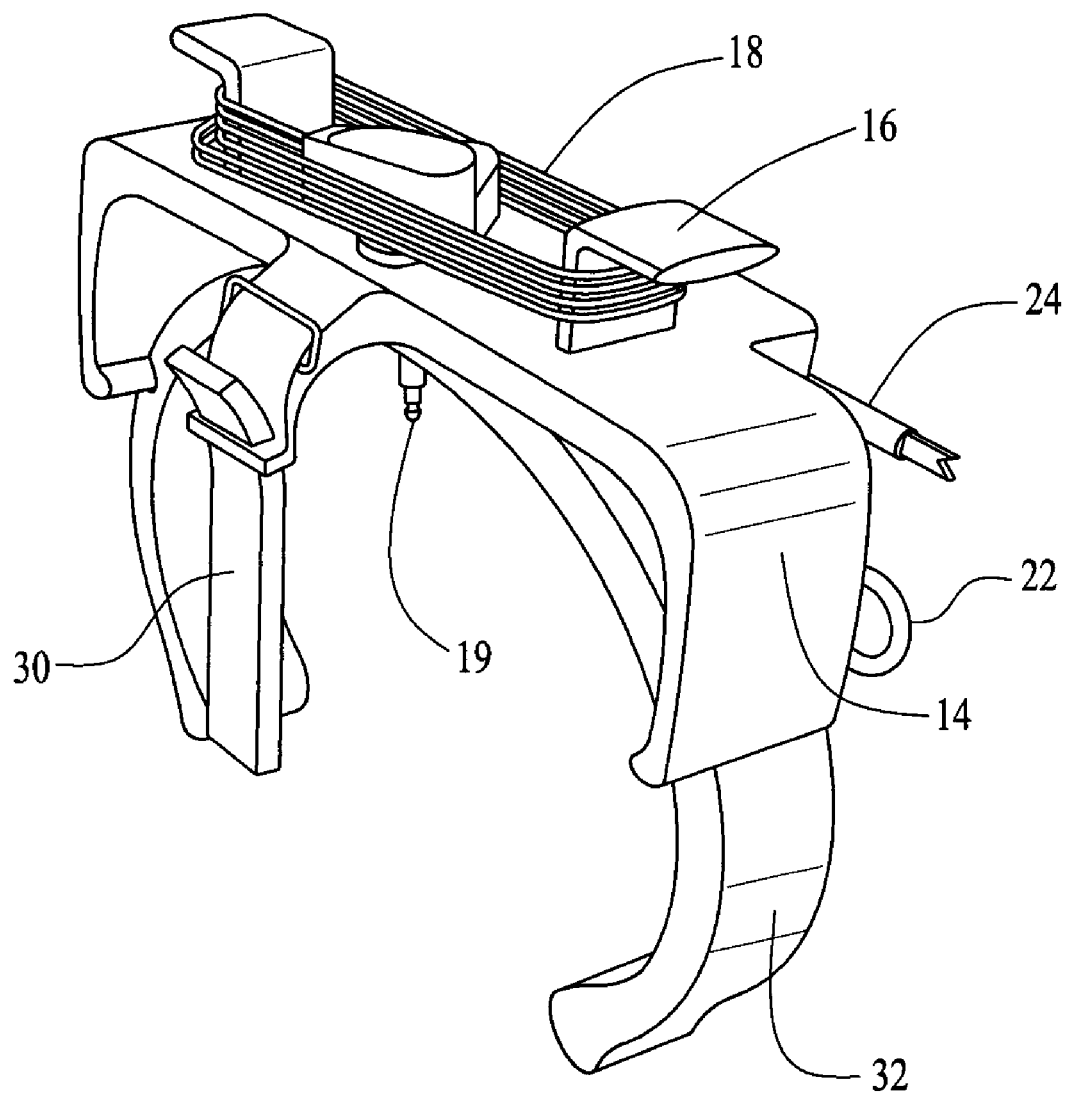
FIG. 5 is a rear perspective view of the caddy stand with a hinged stand and a bracelet arrangement attached.

An electronic apex locator and root length measuring device comprises a display component or unit 10 and a detachable lead caddy 14 carrying electrical leads for use in locating the apex and measuring the root length.

The apex locator display unit 10 is miniaturized to approximately 1" deep, by 2.5" wide, by 1.5" high, having indentations 12 on either side for engagement of the cord caddy stand 14 which is clipped onto the display unit 10 after the display unit is enclosed in a clear plastic zip-lock barrier bag 15. The plug 19 from the lead set is held in a downward position so that it automatically penetrates the plastic barrier bag 15 and is received into a lead connector 17 on the top of display unit 10 as it is secured over the barrier bag 15. Assembly does not compromise the sterility of either the bagged display or the leads on the caddy.

The caddy stand 14, has cord winding posts 16 on its top surface to hold the lead set 18 and clips 20 on its front surface to hold the different lead ends, specifically the ground lip lead 22, the file probe 24, and an accessory file probe 26. On the back surface of the display unit 10 or caddy stand are an optional magnet 28 for attaching the apex locator 10 to a metal surface, a hinged stand 30 that folds out if the unit is to set on a countertop or can be used to attach the unit to a drape 34, and a detachable bracelet arrangement 32 so that the unit can be secured to the clinician's wrist during use. The caddy stand 14 is of a size that easily fits into an autoclave bag for sterilization of the assembled stand 14, the lead 18, and the lead ends 22, 24, 26.

Once the ground lead 22 is placed against the patients lip and one of the probes 24, 26 is placed in contact with a metallic instrument, such as a file or a probe, within the root canal, the depth of the tip of the instrument can be manipulated and the numbers 36 displayed on the face of the apex detecting unit can be viewed until a reading indicative of the apex location is obtained. The position (depth) of the apex can then be indicated by various techniques including sliding a rubber ring along the exposed length of the metallic instrument residing in the root canal and into contact with the biting surface of the tooth receiving the root canal procedure.

While the display on the device is indicated as numbers 36, one skilled in the art will recognize that other visible displays such as graphs, bars or color changes can also be used to indicate the increased electrical conductivity indicative of locating the apex. It is also contemplated that an audible output in place of or along with the visual display may also be provided such as an increase in volume of a sound output or a change in the frequency or other characteristics of an audible output.

I claim:

1. An electronic device for locating the apex of a root canal within a tooth of a dental patient comprising a display component having a display screen for indicating attainment of the apex, at least a first and a second electrical lead connected to the display component, the first electrical lead for placement within the root canal or in electrical contact to an electrically conductive tool placed within the root canal and the second electrical lead for establishing a ground on a conductive portion of the dental patient, one or more mounting structures for placing the display in a location adjacent the patients head, attached to adjacent instrumentation, or attached to the dental practitioner's hand or arm such that the display image is readily visible by the dental practitioner during the apex locating procedure, the improvement comprising a carrier for the first and second leads, said carrier comprising a lead caddy removeably connectable to the display component, the first and second electrical leads mounted on the removeable lead caddy, said lead caddy including means for removeably mounting one or more sensing tools thereto, the caddy also including first and second electrical connectors mateable with first and second electrical connectors on the display component such that when the removeable lead caddy is properly attached to the display component an electrically conductive path is provided between patient contact ends of the leads and electronic components within the display component.

2. The electronic device of claim 1 wherein the lead caddy's first and second electrical connectors comprises a single plug extending outward therefrom, the plug having at least two electrical conductive portions in electrical communication to the first and second leads, the first and second electrical connectors on the display component having a compatible electrical plug for mating with the plug on the lead caddy.

3. The electronic device of claim 1 wherein the lead caddy can be sterilized independently of the display device and the electrical conductive path can be established between the leads on the lead caddy and the display device without compromising the sterility of the assembled electronic device.

* * * * *